United States Patent
Maschke

(10) Patent No.: US 7,238,178 B2
(45) Date of Patent: Jul. 3, 2007

(54) DEVICE FOR PERFORMING LASER ANGIOPLASTY WITH OCT MONITORING

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 159 days.

(21) Appl. No.: 11/058,547

(22) Filed: Feb. 15, 2005

(65) Prior Publication Data

US 2005/0187541 A1    Aug. 25, 2005

(30) Foreign Application Priority Data

Feb. 20, 2004   (DE) .................. 10 2004 008 366

(51) Int. Cl.
*A61B 18/22* (2006.01)
*A61B 18/24* (2006.01)
(52) U.S. Cl. .................. 606/7; 606/15; 607/89
(58) Field of Classification Search .............. 606/7, 606/10–12, 15–18; 607/88, 89
See application file for complete search history.

(56) References Cited

U.S. PATENT DOCUMENTS

| 5,093,877 A | 3/1992 | Aita et al. |
| 5,193,546 A | 3/1993 | Shaknovich |
| 5,496,305 A * | 3/1996 | Kittrell et al. ............... 606/15 |
| 5,921,926 A * | 7/1999 | Rolland et al. ............ 600/407 |
| 6,117,128 A * | 9/2000 | Gregory ........................ 606/7 |
| 6,660,001 B2 * | 12/2003 | Gregory ..................... 606/15 |

FOREIGN PATENT DOCUMENTS

| EP | 0 355 200 A1 | 2/1990 |
| EP | 0 815 801 B1 | 1/1998 |
| EP | 0 885 594 A2 | 12/1998 |

OTHER PUBLICATIONS

"CVX-300® Excimer Laser System", [online], [retrieved on Feb. 19, 2004], Retrieved from http://www.spectranetics.com/cvx/cvx300.html, Spectranetics, 3 pages, Colorado Springs, USA.

* cited by examiner

*Primary Examiner*—A. Farah

(57) ABSTRACT

Device for performing laser angioplasty, in which laser light is beamed via a laser radiation device in the area of a catheter tip, with simultaneous OCT monitoring, for the ablation of plaque. The feed lines for the laser radiation device and the rotating OCT signal lines are disposed in a common catheter sheath, said feed lines leading to an OCT sensor disposed within a ring-shaped window running around the circumference of the catheter sheath, said OCT sensor being disposed at a distance from the laser radiation device.

18 Claims, 1 Drawing Sheet

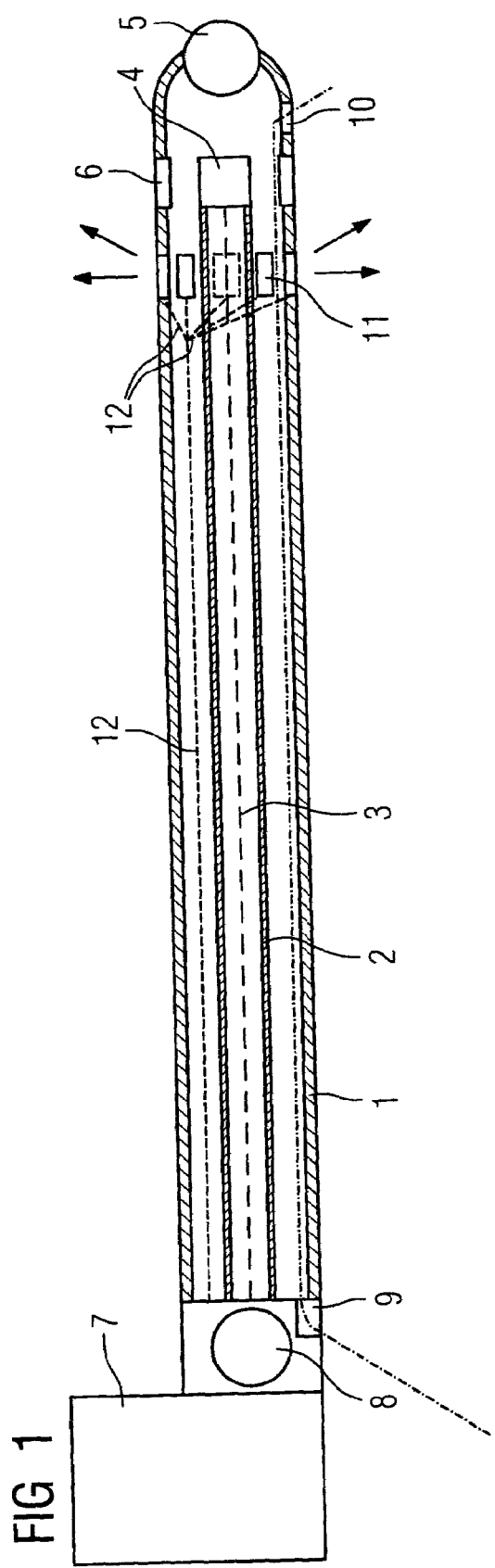
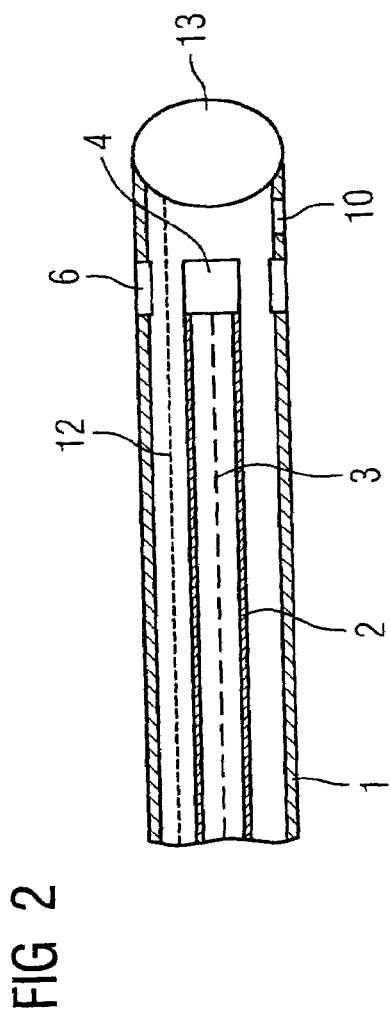
FIG 1
FIG 2

DEVICE FOR PERFORMING LASER ANGIOPLASTY WITH OCT MONITORING

CROSS REFERENCE TO RELATED APPLICATIONS

This application claims priority to the German application No. 10 2004 008 366.5, filed Feb. 20, 2004 which is incorporated by reference herein in its entirety.

FIELD OF INVENTION

The invention relates to a device for performing laser angioplasty, in which laser light is beamed via a laser radiation device in the area of a catheter tip, with simultaneous OCT monitoring, for the ablation of plaque, whereby the feed lines for the laser radiation device and the OCT signal lines are disposed in a common catheter sheath.

BACKGROUND OF INVENTION

Vascular disease, in particular cardiac infarction, is one of the most common fatal illnesses. It is caused by diseases of the coronary arteries (arteriosclerosis), in which the build-up of deposits (arteriosclerotic plaque) causes occlusions in the coronary arteries.

Nowadays, if coronary angiography reveals serious stenoses in the coronary arteries, causing angina pectoris which restricts the patient's capability and/or puts the patient at risk, a PTCA (percutaneous transluminal coronary angioplasty) is carried out in the majority of cases. This is done by expanding the narrowings in the coronary arteries using a so-called "balloon catheter". In recent years, laser angioplasty (PTLA) has also become established for the removal of plaque from coronary arteries, particularly in cases of elongated stenoses (>2 cm), complete occlusion and in-stent restenoses.

Laser angioplasty means the removal of plaque using a thermal or non-thermal laser. The doctor does this by guiding a laser catheter until it reaches the stenosis in the coronary artery. The laser catheter consists of fine optical glass fibers. The laser energy causes photo-acoustic and photochemical processes that enable the plaque to be removed. In the thermal process, a laser balloon catheter destroys calcification by heating it to a temperature of 80 to 100 degrees for 15 seconds. This method is only used vary rarely today. In the non-thermal process, an ultraviolet-pulsed (308 nm) laser (excimer laser) is used. This pulsed laser results in the creation of vapor bubbles within a few hundred microseconds, causing explosive modification of the plaque. This process enables the plaque to be ablated in a controlled manner. The laser angioplasty can then be followed by a further PCTA and/or implantation of a stent.

U.S. Pat. No. 6,117,128 A discloses a device as mentioned above for laser angioplasty, in which an optical fiber for transmitting laser energy from a laser source to the point of treatment, runs in a first lumen of a catheter. A second lumen can accommodate a fiber for an optical coherence tomograph.

U.S. Pat. No. 6,660,001 B2 likewise describes a device as mentioned above, in which a plurality of glass fibers for radiating laser energy from a laser source, and a reflectance fiber, which is closely coupled to the optical reflectance system, are further disposed in the catheter.

A device for laser angioplasty is described, for example, in U.S. Pat. No. 5,093,877, "Optical Fiber Lasing Apparatus Lens" and in EP 0 355 200 A1 "Balloon dilatation catheter with laser cutting capability". An example of a known product is the CVX-300® Excimer Laser System from Spectranetics, Colorado Springs, Colo., USA.

SUMMARY OF INVENTION

The interventions described above are implemented using an angiography device under x-ray monitoring by means of contrast media. The drawback of this method is that the coronary arteries are only shown in two dimensions and only the actual stenosis is shown on the x-ray image. During the intervention it is difficult for medical staff to distinguish between plaque and vascular wall. This increases the risk of the laser being applied to the wrong places, resulting in injury in the form of hemorrhage, damage or perforation/dissection of the vascular wall.

The introduction of an IVUS (intravascular ultrasound) catheter into the vessel enhances the imaging information, yet has the disadvantage that a relatively expensive catheter must also be inserted into the patient and must be removed from the vessel before the balloon catheter is inserted. An IVUS system is described, for example, in DE 198 27 460 A1 and U.S. Pat. No. 5,193,546. The disadvantage of the IVUS solution lies in the limited local resolution of the ultrasound method.

Significantly better local resolution, particularly within close range of the area concerned, is delivered by an OCT catheter which is inserted separately into the vessel.

The OCT (Optical Coherence Tomography) method is described, for example, in U.S. Pat. No. 5,921,926 and EP 0 815 801 B1. The OCT technique works similarly to the imaging ultrasound technique (B-method). The underlying physical principle is based on the Michelson Inferometer.

The disadvantage of this method is that the OCT device must be withdrawn from the vessel each time the laser catheter is inserted.

An object of the invention is therefore to create a device in which laser angioplasty can be carried out with simultaneous OCT monitoring.

This object is achieved according to the invention, in that the OCT signal lines are configured as rotating OCT signal lines that lead to an OCT sensor disposed within a ring-shaped window running around the circumference of the catheter sheath, said OCT sensor being disposed at a distance from the laser radiation device.

The integration, according to the invention, of a laser angioplasty catheter with an OCT (Optical Coherence Tomography) catheter into a single module produces an optimum system for reducing vascular stenoses. The great advantage of this combined catheter lies in the reduction in process stages and in the catheters used. At the same time, a lower x-ray level is required to monitor the catheter implementation. The OCT system images provide important additional medical information with high resolution, particularly at close range over the plaque and the vascular wall. This means that the plaque can be identified, and can be removed by using the laser probe in the right locations with the right amount of energy, and the success of the procedure can then be checked immediately. This combined device thus significantly reduces the known risks of such an intervention.

The OCT sensor, which is preferably configured as a revolving mirror, may be located both in front of and behind the laser radiation device when viewed from the external end of the catheter, whereby the arrangement in front of the laser radiation device has the advantage that the drive shaft for the OCT sensor does not have to be run right through the laser radiation device, said drive shaft being preferably configured as a hollow, flexible drive shaft which also accommodates the OCT signal lines, which are configured as glass fiber lines. If the drive shaft did have to go right through the laser radiation device, this would potentially create problems if said radiation device is a radiating lens which is connected to an external laser light source via an optical fiber line.

The running of the drive shaft through the laser radiation device presents no difficulties, however, if said laser radiation device comprises an outwardly radiating diode array, preferably ring-shaped and circumferential, which is connected to an external control circuit via electrical connection lines. In this case, therefore, it is not external laser light that is fed in, but the laser light that is generated by the laser diode array at the radiation point of the catheter tip. By selectively controlling the individual laser diodes as appropriate, a beam can be aimed in just one specific direction so that plaque deposits can be irradiated completely selectively without simultaneous irradiation of an inner vascular wall that is not coated with plaque.

The catheter sheath may advantageously be provided with inlet and outlet openings at each end for contrast media or irrigation fluid, since an irrigation solution (e.g. physiological saline solution) must be injected in the vicinity of the area to be treated or investigated in order to use both the laser catheter and the OCT catheter.

As well as the disposal of magnets on the catheter tip for magnetic navigation, one embodiment of the device may also be provided with a guidewire running through it.

Finally, the invention also makes provision for an inflatable and preferably multi-chambered balloon, which is used for fixing the catheter and/or for vascular dilatation, to be disposed on the catheter tip. This balloon may be used both for fixing the catheter tip in a required location during the intervention or for additional dilatation of the vessel, thus providing additional mechanical means for breaking up of plaque deposits.

BRIEF DESCRIPTION OF THE DRAWINGS

Other advantages, features and details of the invention are explained in the following description of an exemplary embodiment, on the basis of the diagrams in which:

FIG. 1 shows a schematic longitudinal section through a combined OCT laser angioplasty catheter according to the invention, with an OCT sensor disposed in the catheter tip, and FIG. 2 shows a partial section of the catheter tip of a modified OCT laser angioplasty laser in which the externally generated laser light is transferred to a radiating lens located in the catheter tip.

DETAILED DESCRIPTION OF INVENTION

FIG. 1 is a schematic diagram of a combined OCT laser angioplasty catheter with an outer, flexible catheter sheath 1, inside which is disposed a hollow, flexible drive shaft 2 with integrated glass fiber line 3 as the OCT line. The hollow, flexible drive shaft is used for driving a rotating mirror 4 which forms the OCT sensor, said rotating mirror being disposed in the catheter tip behind a balloon 5 used for fixing the catheter and/or for vascular dilatation. The rotating mirror 4 is located inside a ring-shaped, circumferential output window 6 for the infrared light with which the inner vascular wall is irradiated and which is fed in via the signal lines 3, whereby the reflected light is fed back through the same line and processed at the external end of the catheter in an appropriate evaluation device 7. A rotating coupling for the connections is shown at 8, while 9 represents an inlet opening for feeding in contrast media and irrigation fluid which is transported forward inside the catheter sheath, possibly even inside an additional irrigation fluid line disposed therein, toward an irrigation fluid outlet opening 10. In the exemplary embodiment shown in FIG. 1, the laser radiation device consists of a diode array 11 distributed in a ring shape around the catheter sheath, said diode array being connected, via electrical connection lines 12, to a control circuit disposed on the external processing unit 7, which also permits individual control of specific laser diodes on the diode array 11 and, therefore, allows the laser light beam to be focused laterally. The advantage of using such a diode array for the direct generation of laser light in the output area on the catheter tip is that the drive shaft 2 can be run right through the laser radiation device, making the arrangement as shown in FIG. 1 possible for the first time.

FIG. 2 shows a modified exemplary embodiment of an OCT laser angioplasty catheter according to the invention, in which the laser radiation device is disposed on the catheter tip. The arrangement shown in FIG. 2, in which the balloon 5 is not illustrated, shows a laser lens 13 which is connected to an external laser light source via an optical fiber line 12'. In this case the OCT sensor, i.e. the rotating mirror 4, is adjacent to the external catheter, so that penetration of the laser radiation device is not necessary, which could indeed lead to certain problems in the case of a laser lens.

The invention is not limited to the exemplary embodiments shown. Thus, as well as the arrangement of magnets in the catheter tip for magnetic navigation, a guidewire might also be used, said guidewire being initially inserted into the vessel, under x-ray monitoring, until reaching the target position (stenosis). Then, in such an arrangement with a guidewire, the laser angioplasty catheter with integrated OCT probe according to the invention is pushed forward to the target position, again with x-ray monitoring and possibly using contrast media. When this target position is reached, irrigation fluid for the OCT process is injected and the point at which the plaque is to be removed is observed with high resolution. Laser angioplasty is then carried out on the plaque and the point at which the laser energy was applied is immediately checked using the OCT sensor component. An additional dilatation of the vessel by means of a suitable balloon may then be effected if necessary, as already suggested above.

The invention claimed is:
1. A device for performing laser angioplasty including ablation of vascular plaque by applying a laser, comprising:
 a catheter device having a catheter tip;
 a laser emitting device arranged adjacent to the catheter tip;
 a catheter jacket for accommodating the catheter device;
 a feeding line connected to the laser emitting device;
 an OCT sensor for acquiring monitoring signals arranged in the catheter tip inside a circumferential ring-shaped window in the catheter jacket and at a distance from the laser emitting device; and
 a rotating OCT signaling line for transmitting monitoring signals connected to the OCT sensor, the feeding line and OCT signaling line arranged within the catheter jacket
2. The device according to claim 1, wherein the OCT sensor comprises a rotating mirror.

3. The device according to claim 1, wherein the OCT sensor is arranged behind the laser emitting device relative to a laser emitting direction.

4. The device according to claim 1, wherein the OCT sensor is arranged in front of the laser emitting device relative to a laser emitting direction.

5. The device according to claim 1, further comprising a hollow, flexible drive shall for rotating the OCT sensor.

6. The device according to claim 5, wherein the OCT signaling line is arranged within the drive shaft.

7. The device according to claim 1, wherein the OCT signaling line comprises a glass fiber line.

8. The device according to claim 1, wherein the catheter jacket includes inlet and outlet openings for feeding to respectively discharging from the catheter device a contrast medium or a rinsing fluid.

9. The device according to claim 1, wherein the laser emitting device includes a lens for emitting laser light and the feeding line comprises an optical fiber line for connecting an external laser light source to the lens.

10. The device according to claim 1, wherein the laser emitting device includes a laser diode array connected to an external control device using an electrical connection line.

11. The device according to claim 10, wherein the laser diode array is ring-shaped and encircling the catheter device.

12. The device according to claim 1, further including a plurality of magnets arranged at the catheter tip for magnetic navigation of the device.

13. The device according to claim 1, further comprising a continuous guide wire.

14. The device according to claim 1, further comprising an inflatable balloon arranged at the catheter tip for locating the catheter device and/or for dilating vessels.

15. The device according to claim 14, wherein the balloon has a plurality of inflatable chambers.

16. The device according to claim 1, wherein the catheter tip is insertable to a target position within a patient.

17. The device according to claim 1, wherein the OCT sensor irradiates an infrared light through the circumferential ring-shaped window to an inner vascular wall of a patient for generating the monitoring signals.

18. A device for performing laser angioplasty including ablation of vascular plaque by applying a laser, comprising:
 a catheter device having a catheter tip;
 a laser emitting device arranged adjacent to the catheter tip;
 a catheter sheath for accommodating the catheter device;
 a feeding line connected to the laser emitting device;
 an OCT sensor for acquiring monitoring signals arranged in the catheter tip inside a circumferential ring-shaped window in the catheter sheath and at a distance from the laser emitting device;
 a rotating OCT signaling line for transmitting monitoring signals connected to the OCT sensor, the feeding line and OCT signaling line arranged within the catheter sheath; and
 a magnet arranged at the catheter tip for magnetic navigation of the device.

* * * * *